United States Patent
Bigorra, Llosas et al.

(10) Patent No.: US 8,158,826 B2
(45) Date of Patent: Apr. 17, 2012

(54) CONTINUOUS PROCESS FOR THE PRODUCTION OF MONO- OR DICARBOXYLIC ACID ALKYL AMIDES

(75) Inventors: Joaquin Bigorra, Llosas, Sabadell (ES); Javier Raya, Sant Vicenc dels Horts (ES); Emilio Brau, Balague, Barcelona (ES); Manuel Seva, Castellbisbal (ES); Ivan Francia, Barcelona (ES); Ramon Valls, Barcelona (ES)

(73) Assignee: Cognis IP Management GmbH, Duesseldorf (DE)

( * ) Notice: Subject to any disclaimer, the term of this patent is extended or adjusted under 35 U.S.C. 154(b) by 856 days.

(21) Appl. No.: 12/293,509

(22) PCT Filed: Mar. 9, 2007

(86) PCT No.: PCT/EP2007/002072
§ 371 (c)(1),
(2), (4) Date: Sep. 18, 2008

(87) PCT Pub. No.: WO2007/107256
PCT Pub. Date: Sep. 27, 2007

(65) Prior Publication Data
US 2009/0062565 A1    Mar. 5, 2009

(30) Foreign Application Priority Data
Mar. 18, 2006  (EP) .................................. 06005589

(51) Int. Cl.
C07C 231/02    (2006.01)

(52) U.S. Cl. ........................................... 564/138

(58) Field of Classification Search .................. 564/138
See application file for complete search history.

(56) References Cited

U.S. PATENT DOCUMENTS

| 5,388,644 | A  | 2/1995 | Romocki | .................. 166/268 |
| 6,723,877 | B1 | 4/2004 | Maliszewskyj et al. | ....... 564/215 |

FOREIGN PATENT DOCUMENTS
WO    94/15905    7/1994

OTHER PUBLICATIONS

XP-002391046 & RO 119297B1, 1935.
Wenker, Henry: The Synthesis of Oxazolines and Thiazolines from N-Acyl-2-aminoethanols. In: J. Am Chem. Soc., vol. 75, Jun. 1935, pp. 1079-1080.

*Primary Examiner* — Shailendra Kumar
(74) *Attorney, Agent, or Firm* — Diehl Servilla LLC

(57) ABSTRACT

A continuous process for the production of mono- or dicarboxylic acid alkyl amides is described, which is characterized in that: fresh mono- or dicarboxylic acid is placed into a first reactor (R1) connected with a distillation column (C1) and subjected to a reaction with ammonia or gaseous alkyl amine to form a pre-mixture consisting of mono- or dicarboxylic acid alkyl amide and unreacted mono- or dicarboxylic acid, while the water of condensation is distilled off; said pre-mixture is transferred into a second reactor (R2) also equipped with a distillation column (C2) and subjected to a further reaction with ammonia or gaseous alkyl amine to substantially convert all unreacted mono- or dicarboxylic acid into mono- or dicarboxylic acid alkyl amide; and all unreacted ammonia or gaseous alkyl amine is transferred into the first reactor (R1) to start the amidation reaction.

12 Claims, 1 Drawing Sheet

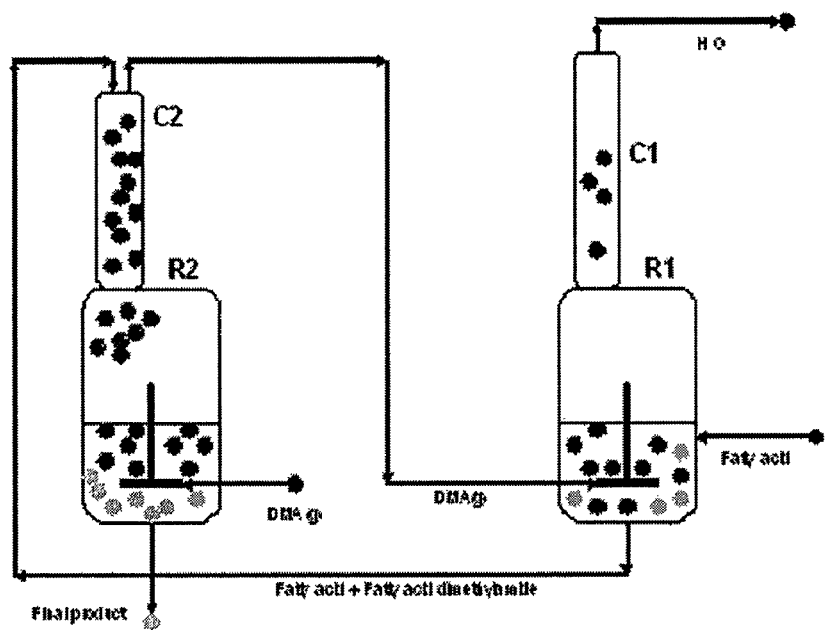
Flow scheme for the amidation of a fatty acid with dimethyl amine (DMA)

CONTINUOUS PROCESS FOR THE PRODUCTION OF MONO- OR DICARBOXYLIC ACID ALKYL AMIDES

CROSS REFERENCE TO RELATED APPLICATIONS

This application is the National Phase entry of PCT/EP2007/002072, filed Mar. 9, 2007, which claims priority to EPO patent application number EP 06005589, filed Mar. 18, 2006, which are incorporated herein by reference in their entireties.

FIELD OF THE INVENTION

The present invention relates to the area of green solvents and covers an improved process for the production of mono- or dicarboxylic acid alkyl amides.

BACKGROUND OF THE INVENTION

Carboxylic acid alkyl amides are well-known intermediates for the manufacture of polymers. Fatty acid alkanolamides, which form a sub-group of this species, are also applied as foam boosters in detergents, while particularly amides, which are based on dimethyl amine and medium chain fatty acids, are used as environmentally friendly, so-called "green" solvents, particularly in agriculture.

Usually, carboxylic acid alkyl amides are obtained from the reaction of triglycerides, carboxylic acids, their esters or acyl halides with alkyl or alkanol amines (see, for example, U.S. Pat. No. 5,388,644). Acyl halides, particularly chlorides, however are difficult to handle, highly corrosive and toxic. In case of esters or triglycerides, alcohols or glycerol are obtained as an unwanted by-product which needs to be separated off and therefore makes the process expensive. The reaction between carboxylic acids and amines usually takes place in the gas phase, which makes it necessary to use closed reactors and high pressure. Due to salt formation, an excess of amine is necessary to achieve an acceptable conversion. Therefore, either non-reacted amine has to be removed after the amidation has been completed, which has a negative impact on the manufacturing costs, or a certain level of free amine in the product has to be accepted which is not always possible, especially in cases where the amides are used as environmentally friendly solvents.

DETAILED DESCRIPTION OF THE EMBODIMENTS

The present invention claims a continuous process for the production of mono- or dicarboxylic acid amides or alkyl amides, comprising:
(a) introducing a mono- or dicarboxylic acid or mixture of acids, and a first stream of ammonia or gaseous alkylamine into a first reactor (R1), said reactor being in fluid communication with a first distillation column (C1);
(b) reacting said acid or mixture of acids in said first reactor with said ammonia or gaseous alkyl amine to form a pre-mixture comprising amide reaction product, unreacted acid and water of condensation, wherein at least a portion of said water of condensation is substantially continuously removed via said first distillation column;
(c) transferring at least a portion of said pre-mixture and a second stream of ammonia or gaseous alkyl amine into a second reactor (R2), said reactor being in fluid communication with a second distillation column (C2);
(d) converting in said second reactor substantially all of said unreacted mono- or dicarboxylic acid to the corresponding amide reaction product;
(e) removing said amide reaction product from said second reactor; and
(f) recycling unreacted ammonia or gaseous alkyl amine from said second reactor to said first reactor.

According to the present invention it is possible for the first time to produce amides from various types of mono- or dicarboxylic acids, including long-chain dimeric acids and all types of short-chain alkyl or hydroxyalkyl amines
  continuously,
  in a closed process without generating unwanted by-products, and
  under stoichiometric and therefore rather economic conditions, which means that none of the compounds is used in excess.

Mono- and Dicarboxylic Acids

A special advantage of the present invention is to produce amides from various types of mono- and dicarboxylic acids. Monocarboxylic acids typically follow general formula (I),

$$R^1COOH \qquad (I)$$

in which $R^1CO$ stands for hydrogen or a linear or branched, saturated or unsaturated acyl radical having 1 to 22 carbon atoms. Typical examples are short-chain carboxylic acids having in total 1 to 5 carbon atoms such as formic acid, acetic acid, propionic acid, butyric acid and pentanoic acid. A second group is formed by the medium and long-chain $C_6$-$C_{22}$ fatty acids, such as caproic acid, caprylic acid, caprinic acid, lauric acid, myristic acid, palmitic acid, palmoleic acid, stearic acid, isostearic acid, oleic acid elaidic acid, linolic acid linoleic acid, ricinolic acid, 12-hydroxystearic acid, conjugated linoleic acid (CLA), gadoleic acid, arachidonic acid, behenic acid, erucic acid and their technical mixtures, such as cocofatty acid, palmoil fatty acid, or tallow fatty acid.

Dicarboxylic acids usually follow general formula (II),

$$HOOC-(X)_a-COOH \qquad (II)$$

in which X stands for a linear or branched, saturated or unsaturated alkylene radical having 1 to 60, and particularly 2 to 10, carbon atoms, with a representing an integer of either 0 or 1. Typical examples are oxalic acid, malic acid, fumaric acid, glutamic acid, adipic acid, 1,10-decandioic acid, 1,12-dodecandioic acid and the so-called dimeric acids, which are obtained from the oligomerisation of long-chain unsaturated fatty acids, such as oleic or erucic acid.

Alkyl and Hydroxy Alkyl Amines

The process according to the present invention also includes the advantage to allow the use of ammonia and of all types of short-chain alkyl amines under the condition that they can be evaporated without decomposition at temperatures below 200° C. Typically said alkyl amines follow general formula (III),

$$R^2-\underset{\underset{R^3}{|}}{\overset{\overset{R^4}{|}}{N}}-R^3 \qquad (III)$$

in which $R^2$ stands for a linear or branched alkyl radical having 1 to 6 carbon atoms, $R^3$ and $R^4$, independently from each other, represent hydrogen or also linear or branched alkyl radicals having 1 to 6 carbon atoms. Typical examples are methyl amine, dimethyl amine, trimethylamine, ethylamine, diethylamine, triethylamine, propylamine, dipropylamine, tripropylamine, methylethylamine, and their mixtures.

In a preferred embodiment of the present invention, $C_6$-$C_{22}$ fatty acids are reacted with dimethyl amine (DMA).

Manufacturing Process

The process according to the present invention is illustrated in FIG. 1, which shows a preferred example for the production of fatty acid dimethyl amides. A major advantage of the invention is that the reaction partners are reacted in stoichiometric amounts, which means that one mole of alkyl amine is reacted with one mole of monocarboxylic acid or 0.5 mole of dicarboxylic acid. With the exception of condensation water, which is separated off from the reaction mixture in order to shift the balance to the product side, no by-products are formed, nor are measures necessary for re-cycling excess amines or acids. Amidation takes place in two corresponding reactors which form a closed system. The reaction is typically conducted at a temperature in the range of about 150 to about 250° C., and preferably about 200 to about 220° C., while the pressure typically ranges from about 1 to about 5, preferably about 1.5 to about 2 bar.

The first reactor serves for the production of a pre-mixture of mono- and dicarboxylic acids and their alkyl amides. For this purpose, fresh mono- or dicarboxylic acid (or even their mixtures) are placed into the reactor (R1). Gaseous alkyl amine—preferably gaseous DMA—is introduced into the reactor, preferably by means of nozzles, or simply by bubbling through the liquid acid. The amidation takes place under vigorous stirring. The water of condensation is distilled off via column C1 and cooled outside of the reactor. Once the acid number has decreased to a value of from about 20 to about 90, and preferably from about 40 to about 70% by weight, the pre-mixture thus obtained leaves reactor R1 and enters the top of column C2 which is connected to reactor R2. Said reactor serves to complete the amidation. While the pre-mixture drops down through column C2, gaseous alkyl amine is led in counter-current to react with the free fatty acid in the pre-mixture. The mono- or dicarboxylic acid alkyl amides are collected at the bottom of the reactor and may be recycled back to the bottom of column C2 to ensure that all fatty acid has been converted. Water formed during the condensation is distilled off via column C2. The product is drawn from the reactor when the acid value has reached the desired value, usually a number of less than 6. Any gaseous alkyl amine which has not reacted with the free fatty acid in the pre-mixture is used to feed reactor R1 in order to close the cycle. The mono- or dicarboxylic acid alkyl amide thus obtained can be subjected to standard purification procedures, such as washing, deodorization, etc.

In a preferred embodiment the gaseous alkyl amine is produced in situ from its aqueous solution. For this purpose said aqueous solution, e.g. an aqueous solution of DMA comprising about 60% by weight of water, is fed into the middle of a standard fractionation column. Typically, the conditions within the column are about 120 to about 140° C. and about 1.5 to about 2.5 bar, while the temperature at the top of the column lies in the range of about 50 to about 60° C. While the water is collected at the bottom, the gaseous amine leaves the top of the column and is directly introduced into reactor R2.

What is claimed is:

1. A continuous process for the production of mono- or dicarboxylic acid amides, comprising
    (a) introducing a mono- or dicarboxylic acid or mixture of acids, and a first stream of ammonia or gaseous alkylamine into a first reactor (R1), said reactor being in fluid communication with a first distillation column (C1);
    (b) reacting said acid or mixture of acids in said first reactor with said ammonia or gaseous alkyl amine to form a pre-mixture comprising amide reaction product, unreacted acid and water of condensation, wherein at least a portion of said water of condensation is substantially continuously removed via said first distillation column;
    (c) transferring at least a portion of said pre-mixture and a second stream of ammonia or gaseous alkylamine into a second reactor (R2), said reactor being in fluid communication with a second distillation column (C2);
    (d) converting in said second reactor substantially all of said unreacted mono- or dicarboxylic acid to the corresponding amide reaction product;
    (e) removing said amide reaction product from said second reactor; and
    (f) recycling unreacted ammonia or gaseous alkyl amine from said second reactor to said first reactor.

2. The process of claim 1, wherein said monocarboxylic acids are represented by formula (I),

wherein R1 is hydrogen, or a linear or branched, saturated or unsaturated alkyl group having 1 to 22 carbon atoms.

3. The process of claim 1, wherein said dicarboxylic acids are represented by formula (II),

wherein X is a linear or branched, saturated or unsaturated alkylene group having 1 to 60 carbon atoms, and a is either 0 or 1.

4. The process of claim 1, wherein said alkylamine is represented by formula (III),

wherein $R^2$ is a linear or branched alkyl group having 1 to 6 carbon atoms, and $R^3$ and $R^4$ are independently hydrogen, or linear or branched alkyl groups having 1 to 6 carbon atoms.

5. The process of claim 1, wherein said carboxylic acids are C6-C22 fatty acids and said amine is dimethylamine.

6. The process of claim 1, wherein said carboxylic acids and said alkyl amine are reacted in stoichiometric amounts.

7. The process of claim 1, wherein said reaction step (b) and said converting step (d) are each independently conducted at one or more temperatures of from about 150° to about 250° C.

8. The process of claim 1, wherein said reaction step (b) and said converting step (d) are each independently conducted at one or more pressures of from about 1 to about 5 bar.

9. The process of claim 1, wherein said gaseous alkylamine is generated in situ by fractionation of the respective aqueous solution.

10. The process of claim 1, wherein said pre-mixture contains from about 10% to about 60% by weight of amide reaction product.

11. The process of claim 1, wherein said pre-mixture and said gaseous alkylamine are fed into said second reactor R2 in counter-current fashion.

12. The process of claim 1, wherein said unreacted gaseous alkylamine is removed from the reaction mixture in said second reactor R2 through said second column C2.

* * * * *